United States Patent [19]

Robinson

[11] 4,287,222

[45] Sep. 1, 1981

[54] METHOD FOR PRESERVING PLANT MATERIAL

[76] Inventor: Ruth A. Robinson, 807 S. Warson Rd., St. Louis, Mo. 63124

[21] Appl. No.: 88,296

[22] Filed: Oct. 26, 1979

[51] Int. Cl.$^3$ ............................................. A01G 5/06
[52] U.S. Cl. ........................................... 427/4; 428/22
[58] Field of Search ............................... 427/4; 428/22

[56] References Cited

U.S. PATENT DOCUMENTS 3,573,082   3/1971   Fremling .................................. 427/4
3,895,140   7/1975   Sheldon ................................... 427/4

Primary Examiner—Sam Silverberg
Attorney, Agent, or Firm—Kalish & Gilster

[57] ABSTRACT

A method for preserving cut plant material comprising immersing, within a pressure vessel, the particular material in a treatment agent constituted of glycerin, ethylene glycol, diethylene glycol, triethylene glycol or mixtures thereof; said treatment agent having a specific gravity within the range of 1.10 and 1.16; there being a suitable dye provided with said agent. The immersed material is subjected to an applied pressure greater than atmospheric, as within the range of 5 to 40 psi; but under ambient temperature and humidity, the material being maintained under such pressure for a predetermined period dependent upon the applied pressure for absorption of the agent and dye. The material is then washed and thereafter permitted to be dry under room conditions.

9 Claims, No Drawings

METHOD FOR PRESERVING PLANT MATERIAL

BACKGROUND AND SUMMARY OF THE INVENTION

This invention relates in general to plants and the like and, more particularly, to a method for preserving leaves, stems and plant parts, including some inflorescences.

Heretofore, various efforts have been attempted for preserving plant material such as set forth in U.S. Pat. No. 2,057,413 which discloses the subjection of plant cuttings, roots, bulbs and the like to an emulsion formed from carnauba wax and a salt of oleic acid. The emulsion dries to form a coating of predetermined thickness which protects the plant material, particularly incident to transplantation. In the U.S. Patent to Koropp et al, No. 1,484,656, there is revealed a method which comprehends firstly drying the plant material, then treating the same with a softening and preserving composition which may be a solution of 10 parts glycerin, 89 parts water, and 1 part formalin. The glycerin is utilized for the purpose of softening the texture of the dried material. Following such preliminary treatment, coloring matter is applied upon the exterior surfaces of the plant, such as by a flat oil paint. Said patent further shows that treatment may also involve applying varnish to protect the flat colors and to prevent drying out; with the paint and varnish serving to seal the pores and protect the glycerin against change in moisture content. Other prior art relating to such material has been directed toward bleaching and/or dyeing of plant material, such as U.S. Pat. No. 2,026,873 wherein dried and bleached ruscus is primarily treated with an emulsified solution of glycerin and water-soluble sulphonated vegetable oils for softening purposes; with there being also an included vegetable gum intended to prevent the glycerin from drying out in hot weather and counteractive of the tendency of the glycerin to render the ruscus translucent. In U.S. Pat. No. 2,083,191 there is disclosed the use of primary aliphatic alcohols, having less than 3 carbon atoms, and a pressure of from 3 to 7 psi as developed by a temperature within the range of 115° to 145° F. for bleaching the plant material. The alcohol actually serves as a dehydrating agent.

Thus, in those instances wherein an appearance comparable to the natural appearance of the plant material has been sought, for the most part, the material has been preliminarily dried and/or bleached and glycerin has been utilized solely as a secondary treatment agent for the softening of the material. Various expedients have been adopted to prevent the loss or drying out of the glycerin under varying atmospheric conditions.

Therefore, it is an object of the present invention to provide a method for treating plant material which preserves same in a condition paralleling the appearance of its natural, living state, and with closely comparable physical characteristics, such as color, texture or "feel", shape, as well as pliability.

It is an object of the present invention to provide a method for treating live plant material which does not necessitate drying the same for processing and which does not entail deliberate bleaching.

It is another object of the present invention to provide a method of the character stated which has broad application in that it is efficacious for treating myriad types of leaves, stems, other plant parts, inflorescences, etc. according a user a most substantial range of choice in order to provide plant material for a predetermined purpose, such as, for decorative or ornamental purposes, as well as for educational, expositional, and sentimental purposes.

It is another object of the present invention to provide a method of the character stated, the practice of which does not require highly developed skill, but rather being one that may be engaged in by the average individual.

It is a further object of the present invention to provide a method for preserving live plant material whereby the processed material may be placed in water without damage so that the same can be artistically combined with fresh plant cuttings and flowers for display purposes and may be usable repeatedly in such fashion.

It is another object of the present invention to provide a method of the character stated which accords the treated plant material an indefinite life without diminution in its natural-like appearance and other characteristics.

It is a still further object of the present invention to provide a method of the character stated which is especially suited to treat plant leaves whereby the leaf structure is maintained with high fidelity thereby rendering the same particularly apt for scientific and educational usage.

It is another object of the present invention to provide a method for treating cut plant material which is economical in performance and which requires but limited, inexpensive equipment for practice, possessing an inherent simplicity.

DESCRIPTION OF THE INVENTION

The method of this invention essentially comprises providing a polyol, such as glycerin, ethylene glycol, diethylene glycol, or triethylene glycol, as well as mixtures thereof, as a treatment agent having an optimum specific gravity of between 1.10 and 1.16; the plant material being submerged or immersed therein within a hermetically sealable vessel. A compatible dye is included in the treatment agent to offset the natural degradation of the plant chlorophyll as the material ages. Pressure in excess of atmospheric pressure is applied, as by means of an air compressor, to the vessel contents which pressure is maintained for a predetermined time interval permitting completion of the requisite processing. The applied pressure causes the agent to reliably fully penetrate the cells and pores of the material being treated, assuring absorption thereby. Upon removal of the treated plant material from the vessel, it is washed in cool to warm water and then permitted to dry at the ambient temperature. The entire process may be effected at the obtaining room temperature so that the critical features of the method are the maintenance of the specific gravity of the treatment agent; the application of pressure without the necessity of temperature elevation; the omission of any preliminary drying of the plant material, as well as the obviating of any steps for intentionally bleaching same.

It will be seen that the present method is accomplished in a most simple manner with a minimum of economically obtainable equipment. The determination of completion of the process is made by visual inspection of the material, such as by the backside of leaves having a metallic-like sheen after washing and while still wet. If the material has a "wet" or translucent appearance, overprocessing or overtreatment is indicated. Many of the beneficial aspects of this method will become all the more apparent from the following.

The plant material which may be processed by the present invention is indeed most extensive comprehending leaves, leaf sprays, grasses and plant parts, such as stems, as well as including some inflorescences, which latter would include heather and Bells of Ireland. The following is but a partial list of the material which has been processed successfully through utilization of the present invention:—astilbe; beech; camellia, canna, coral bells; fern—all types; funkia; golden rain; locust; iris; lemon; Lilly of the Valley; magnolia; mountain ash; ginger; Ti leaves; palm—all kinds; peony; rhododendron; violet; Ivy—all kinds; Myrtle; pachysandra; holly—all types; Lilly—all kinds; pines; hemlock; boxwood; yews; protea; ming fern; rose; dogwood; honeysuckle; viburnum—all types; asparagus fern—all types; heather—leaves, stems and flowers; grass—all types; grass seed; magnolia pods; fruit tree leaves—all types; mosses; evergreens and deciduous tree leaves—all types; catonia aster; arborvitae; mahonia; spirea; Bells of Ireland (flower sprays).

The selected plant material for preservation is subjected to a treatment agent having humective properties, which is selected from the class of polyols comprising glycerin, etylene glycol, diethylene glycol, triethylene glycol, or mixtures thereof. Such agents as absorbed by the live plant material do not dry or bleach the same but serve to maintain the same in a state which approximates the natural condition thereof and with the expected characteristics of such material remaining stable. As a treatment agent glycerin is provided in a solution, approximately 40% to 60% by volume of glycerin, which may be U.S.P. 96% glycerin. A solution of 50% glycerin at 20° C. possesses a specific gravity of 1.1267 which is the preferred specific gravity of the treatment agent for the present invention. If technical grade glycerin is utilized a relatively greater amount of water may be needed since such glycerin has normally a specific gravity of 1.2653 so that lowering thereof is necessary. After each practice of the present method, the specific gravity of the treatment agent must be checked and, if necessary, readjusted to a specific gravity within the range of 1.10 to 1.16. Frequently, the dispelled exudates from the treated material will tend to lower the specific gravity of the treatment agent. With glycerin solutions there would only be the need to add additional glycerin to effect restoration to within the critical specific gravity range.

Ethylene glycol, diethylene glycol and triethylene glycol must be used in a nondiluted state as the specific gravities thereof are such as to fall below the crucial range if the same are diluted. The specific gravity of ethylene glycol is 1.1155; that of diethylene glycol is 1.1184; and that of triethylene glycol is 1.1254. It should be understood that the treatment agent may comprise combinations of the glycols and that glycerin may, if necessary, be mixed with one of the said glycols or with a combination thereof to assure a specific gravity within the desired, stated range.

Desirably, a dye is incorporated into the processing solution for absorption by the plant material which may enhance the existing color, introducing new color for creating a pleasing effect, or merely serving to effectively offset diminution in the natural color by reason of the degradation or oxidation of the chlorophyll, as the material ages. A broad range of dyes may be utilized for this purpose, such as vegetable dyes, organic dyes or inorganic dyes. Understandably, those dyes which after processing of the plant material result in the process material being color fast to sunlight are preferred. The quantity of dyes utilized is basically a matter of choice since the practitioner will use the amount adequate to bring about the particular shade preferred. Among the dyes which yield the desired results as to shade and color fastness as to light are the TOPMOST* trademark and FRENCH** food color dyes which are exemplary of the useful vegetable dyes.

*TOPMOST is a trademark of General Grocer Co. of St. Louis, Missouri.
**FRENCH is a trademark of the R. T. French Co. of Rochester, New York.

Another group of readily available dyes which are efficacious for the present method are dyes produced by Pylam Products Co., Inc. of Queens Village, N.Y., such as PYLAM Fast Acid Green 923762; PYLAM Olive Green 812762; PYLAM Fast Acid Green A16; 1 PYLAM Green 992; PYLAM Yellow 1712, etc. The various green shades provided by these dyes may, of course, be suitably modified as by the incorporation of red or yellow dyes in accordance with well-knwon color mixing techniques. Thus, as an example only, a vegetable green dye may be modified with a vegetable red dye wherein the resultant solution would have a concentration of approximately 3 tablespoons of green dye and 18 drops of red dye per quart. It is apparent that the particular usage of dyes is a matter of selection and preference by the particular individual practicing the method. It would, therefore, suffice to merely state that in the present invention providing a dye is solely for the purpose stated, namely to offset the loss of coloration through the deterioration of the plant chlorophyll. It is to be understood that the particular dyes used are not a part of the present invention.

The plant material, such as a leaf, to be treated in accordance with the present invention is placed in a vessel and then the glycerin, glycol, or glycerin-glycol treatment agent, preferably embodying a dye, as the case may be and as above described, is charged to the vessel to a depth sufficient to submerge the plant material. If necessary, a suitable hold-down wire mesh may be used to assure complete immersion of the material. Only a limited quantity of the agent is needed. The vessel, although hermetically sealed, is adapted to permit the introduction of air under pressure and is, therefore, suitably connected to a source of air under a pressure greater than atmospheric, by use of an air compressor, whereby the contents of the vessel are pressurized. The pressure is applied without temperature elevation, with the method being carried out at ambient or room temperature, productive of full penetration of the agent within the material being treated. In addition to promoting complete penetration, the applied pressure produces consistently excellent results in minimum treatment time relative to methods heretofore practiced. It has been known that prior to the present invention, leaves and other plant material have been treated by submergence in a 50% glycerin solution or by placing the stems with the leaves in a vessel containing a 33% glycerin solution for absorption through the stems. However, the material so processed required extensive periods of treatment, as in the order of a plurality of weeks, but without any assurance of beneficial results.

Earlier techniques were erratic and unreliable, even with leaves of the same type. The lack of resort to appropriate pressure heretofore caused material to require extensive processive time as in the order of several weeks and yet not assuring of desirable results so that much material was wasted and at other times a complete failure was encountered. Many leaves that may now be processed by the present method could not be processed at all by use of earlier methods. By utilization of the pressure as taught by the present method, the range of material amenable to processing is most extensive, as set forth hereinabove and with results being quite dependable so that loss or wastage of material, to all intents and purposes, are eliminated and with a much enhanced quality in the finished product. Leaves processed by current methods were susceptible to drying in a room with low humidity and acceptable colors could not be incorporated. By use of the present method with the applied pressure penetration of the treatment agent, the accompanying dye is substantially complete and a much improved range of colors can be used so that problems which beset practitioners of older methods are resolved by the present invention.

The particular pressure applied may vary depending upon the material being treated, with the following factors being considered by the practitioner for determining the amount of pressure required, such as the tenderness of the material, the thickness thereof, the thickness of cuticles in leaves, and the degree of freshness, that is, how long ago the same may have been cut or gathered. Optimum results have been obtained within a range of 18 to 24 psi, but dependent upon age, condition, and variety resort to pressures as low as 5 psi and as high as 40 psi have been used. As stated, the 18 to 24 psi range has proved the range of choice for a high level of quality in the treated product. It is apparent that with lower pressures an increased time interval is requisite so that below 5 psi the practice of the present method is not economic or dependable.

The period during which pressure is applied, of course, relates to the amount of pressure involved, so that pressure and time are inversely proportional, with higher pressures requiring shorter times and lower pressures requiring longer times. However, as developed hereabove, the application of pressure is critical since mere soaking of the plant material for an indefinite period of time at ambient or atmospheric pressure would not bring about the requisite penetration which distinguishes plant material treated by the present invention from that subjected to current processes.

In order to determine whether the particular pressure has been applied for a sufficient period, the material is visually inspected, to note whether the same possesses a metallic-like sheen and is opaque after washing and while still wet. If such condition obtains, the processing is completed. Overprocessing is readily detected by the material having a translucent and, hence, unnatural quality.

In general, it has been found that the period for subjection under pressure is normally within the range of 3 to 5 days, but on rare occasions, with certain material, a period approaching 7 days may be required. But, in more than the majority of the cases utilizing pressure within the optimum range 18–24 pounds, 3 days is usually adequate. Exemplary of the time/pressure relationship for producing the beneficial results of the present invention are the following:

Leatherleaf fern, 24 psi for 3 days;
Heather, including the stems and the flowers, 20 psi for 3 days;
Ming fern, freshly cut, 24 psi for 3 days;
Rose leaves, as cut, 10 psi for 3 days;
Rose leaves, new and tender, 19 psi for 2 days;
Corabell leaves, as cut, 20 psi for 2 days;
Boxwood, with heavy cuticle, 40 psi for approximately 7 days; and
Fresh tender ferns, 5 psi for 4 days or 15 psi for 2 days.

It is to be recognized that the foregoing are merely examples and are submitted for illustrative purposes only and without limitation since the respective list set forth hereinabove demonstrates the breadth of the field of application of this invention. Thus, the utilization of pressure under the optimum ranges has brought about a truly remarkable reduction in treatment time which prior to the present invention was measured in weeks rather than days. It is indeed observed that with pressure increase the amount of time will be reduced since the pressure and time factors are inversely proportional. Prior to the present invention, live plant material in actual practice was not generally subjected to pressure in excess of 7 psi, whereas the foregoing has clearly taught that pressure generally within the range of 18 to 40 psi has proved most beneficial from a substantive standpoint as by assuring of requisite penetration of the treatment agent, as well as from an economic standpoint in representing marked savings of time. Leaves are usually processed with the associated stems or branches; and different sizes of the same material and different varieties thereof may be concurrently processed if desired.

After termination of the pressure period, the plant material is removed from the vessel, washed in cold to warm water, and then permitted to dry at room temperature in any convenient manner, such as by suspension from a line, or mere deposition upon screens, paper or the like. The now dried material is available for the intended usage. As indicated above, the treated material retains its natural appearance and texture so that one may not readily observe any distinctions when such material is used in conjunction with freshly cut or natural plant material. There has been no physical insult or injury to the plant material so that its visible structural and physical characteristics are unchanged.

It will be seen that the present method does not seek to bleach the plant material but rather to promote its normal condition as to form, color, and substance. It has been known that methyl and ethyl alcohol have been used for penetrating the fibers of the plant or foliage to remove all traces of chlorophyll, the source of the green coloration for leaves and the like, but in the present invention by using glycerin and/or glycols the material is neither bleached nor dried. By reason of the retention of the physical, quasi-natural characteristics of the plant material, the present method has wide application in the decorative or ornamental fields, as for floral arrangements, as well as for scientific or educational purposes. Material so treated has indeed an indefinite life and can be placed in water, as in mingling with fresh cuttings, without sustaining any damage whatever; and during its life is not subject to drying so that it continuously maintains its fresh appearance. Thus, the problems encountered heretofore requiring exterior sealing coats is obviated.

If preferred, for solution longevity, a suitable anti-fungus and/or anti-bacterial agent may be dissolved in the processing solution. Such chemicals serve solely to preserve the life of the treatment solution and are not necessarily for plant material processing. Such agents are well-known but for purposes of exposition, reference may be made to benzolkonium chloride which has proved most efficacious. This last-mentioned chemical may be added to the processing solution as in a quantity of 1 teaspoon of concentrate of 17% aqueous solution per quart of processing solution for bacteriostatic purposes. But, as stated, numerous other well-known agents may be utilized for such ends.

The plant material may be washed prior to subjection to processing if such may be extremely dirty, but this is rarely necessary. However, if washing is required, the material should be well shaken after washing to dispose of excess moisture. Also the treatment solution should be checked as to specific gravity to make certain that there has been no inadvertent decrease below the desired range by reason of the dampness of the material being processed.

Although, as set forth hereinabove, consistently excellent results are obtained by utilizing the processing solutions at ambient temperatures, when the plant material is relatively aged and tough or possessing a heavy cuticle, it has been discovered that treatment thereof may at times be slightly facilitated, and with a limited reduction processing time by warming the treatment solution prior to use to a temperature between 105°–115° F. However, with such warmed solutions, the same are allowed to return to ambient temperatures as the processing continues. Maintaining the relatively higher initial temperature provides no advantage and may at times be detrimental, causing the material to lose its natural crispness and become soft and mushy. Warming the solution to temperatures above the aforesaid limited range yield negative results. Thus, the gain in resorting to warming the solution is of limited benefit with the aforesaid type of material but is unnecessary and wasteful of time when the material being treated is of normal character.

Although plant material, which is relatively old or possesses a heavy cuticle is generally more difficult to process than the usual relatively fresh material, the same are amenable to the present invention. But, it has been discovered that the addition of a small amount of petroleum sulfonates, as in a quantity of 1 to 4 teaspoons of a 1% solution per quart of processing solution, is effective in preparing the material for more readily responding to treatment by the method. Other wetting agents may be used with equal efficiency. Another method of pre-treating old, heavy plant material without adding a petroleum sulfonate to the treatment solution would comprise pre-soaking such material in a solution of 4 teaspoons of petroleum sulfonate in 1 quart of water for approximately 1 hour or pre-soaking the same in plain water for 3 to 4 hours. As stated, these preliminary procedures are set forth for instructional purposes but, as indicated above, are only suggested with the material described.

Actually, the use of a petroleum sulfonate, or any other wetting agent, is contra-indicated in routine usage, that is with relatively fresh material, since utilization of such agents renders most material translucent and thus imparts an unnatural appearance to the processed material.

Having described my invention, what I claim and desire to obtain by Letters Patent is:

1. A method of processing cut plant material comprising immersing the plant material to be processed in a liquid treatment agent comprising a polyol or mixtures thereof and having a specific gravity within the range of 1.10 to 1.16, subjecting the immersed plant material to a pressure within the range of 5 psi. to 40 psi. under ambient temperature for a time interval of between 2 to 7 days for absorption of the agent in the material, then withdrawing the plant material from the pressurized immersed state, and then permitting the withdrawn plant material to dry under ambient pressure and temperature.

2. A method of processing cut plant material as defined in claim 1 and further characterized by the polyol being from the class consisting of glycerin, ethylene glycol, diethylene glycol and triethylene glycol and mixtures thereof.

3. A method of processing cut plant material as defined in claim 1 and further characterized by the treatment agent being constituted of a solution of 40% to 60% glycerin and the balance being water.

4. A method of processing cut plant material as defined in claim 1 and further characterized by the treatment agent being undiluted and from the class consisting of ethylene glycol, diethylene glycol, triethylene glycol and mixtures thereof.

5. A method of processing cut plant material as defined in claim 1 or claim 2 and further characterized by said agent containing a predetermined quantity of a dye suitable for counteracting the normal loss of color through degradation or oxidation of plant chlorophyll through aging.

6. A method of processing cut plant material as defined in claim 1 or claim 2 and further characterized by the applied pressure being within the range of 18 psi to 24 psi and the interval of application of such pressure being 3 to 5 days.

7. A method of processing cut plant material as defined in claim 1 and further characterized by said material being washed in water subsequent to being withdrawn from immersion in the treatment agent.

8. A method of processing cut plant material as defined in claim 1 and further characterized by the treatment agent being a solution of approximately 50% glycerin having a specific gravity of 1.1267.

9. A method of processing cut plant material as defined in claim 1 and further characterized by there being no adjustment of specific gravity during the performance of the method.

* * * * *